United States Patent [19]

Kyle et al.

[11] Patent Number: 5,407,957

[45] Date of Patent: Apr. 18, 1995

[54] PRODUCTION OF DOCOSAHEXAENOIC ACID BY DINOFLAGELLATES

[75] Inventors: David J. Kyle, Catonsville; Sue E. Reeb; Valerie J. Sicotte, both of Baltimore, all of Md.

[73] Assignee: Martek Corporation, Columbia, Md.

[21] Appl. No.: 479,135

[22] Filed: Feb. 13, 1990

[51] Int. Cl.⁶ .................. A23D 9/00; C12P 7/64; C07C 69/52; A61K 31/225

[52] U.S. Cl. .................. 514/547; 426/33; 426/601; 560/205; 435/134; 514/549; 514/552

[58] Field of Search .......... 435/134, 136; 560/205, 560/190, 191; 426/33, 601; 514/549, 552, 547

[56] References Cited

U.S. PATENT DOCUMENTS

| | | | |
|---|---|---|---|
| 3,854,240 | 12/1974 | Oldham et al. | 47/114 |
| 4,485,173 | 11/1984 | Gierhart | 534/134 |
| 4,670,285 | 6/1987 | Clandinin et al. | 426/602 |
| 4,752,618 | 6/1988 | Mascioli et al. | 514/549 |
| 4,792,418 | 12/1988 | Rubin et al. | 554/186 |
| 4,843,095 | 6/1989 | Rubin | 514/558 |
| 4,868,001 | 9/1989 | Maruta | 426/623 |
| 4,874,629 | 10/1989 | Chang et al. | 425/601 |
| 4,911,944 | 3/1990 | Holub | 426/635 |
| 4,960,795 | 10/1990 | Salte et al. | 514/560 |
| 4,963,385 | 10/1990 | Antrim et al. | 426/602 |
| 5,013,569 | 5/1991 | Rubin | 426/585 |
| 5,130,242 | 7/1992 | Barclay | 435/134 |

FOREIGN PATENT DOCUMENTS

| | | |
|---|---|---|
| 0231904 | 8/1987 | European Pat. Off. .......... 426/417 |
| 0276982 | 8/1988 | European Pat. Off. . |
| 0404058A2 | 12/1990 | European Pat. Off. . |
| 0459744 | 12/1991 | European Pat. Off. . |
| 63-295527 | 1/1988 | Japan . |
| 80250 | 3/1989 | Japan . |
| 1196255 | 8/1989 | Japan . |
| 2013388 | 1/1990 | Japan . |
| 22061881 | 1/1989 | United Kingdom . |
| 8900606 | 1/1989 | WIPO . |
| 9012858 | 11/1990 | WIPO . |
| 9013656 | 11/1990 | WIPO . |
| 9107498 | 5/1991 | WIPO . |

OTHER PUBLICATIONS

Sonnenborn et al. (1982) *Biochem. Biophys Acta*, 712, 523–534.
Yongmanitchai (1989) *Process Biochem.*, 24(4), 117–125.
Liu et al. (1987) *Pediatr. Res.*, 22(3) 292–296 in *Biol. Abstra* 84(10), 760, Abst #100840.
Tunis et al. (1990) *Am. J. Clin. Nutr.*, 51, 994–1000.
Hanson et al. (1988) *Appl. Microbiol. Biotechnol.*, 28, 240–246.
Ackman et al. (1968) *J. Fish, Res. Bd. Can.*, 25(8), 1603–1620.
Pohl et al. (1979) "Marine Algae in Pharmaceutical Science", Hoppe et al., eds., Berlin/N.Y., de Gruyter, pp. 473–523.
Ben-Amotz (1985) *J. Phycol.*, 21, 72–81.
Henderson et al., (1988) *Phytochem*, 27(6), 1679–1683.
Pohl (1981) "CRC Handbook of Biosolar Resources", Mitsui et al., eds., pp. 383–404, Fla., CRC Press.
Kaskins et al., (1964) *Can. J. Microbiol.*, 10, 187–195.
Ervin (1973) "Lipids & Biomembrane of Eukaryotic Microorganissm", pp. 41–143, N.Y., Acad. Press.
Tyrell (1967) *Can. J. Microbiol.*, 13, 755–760.
Aaronsson et al. (1980) "Algae Biomass", pp. 575–601, Shelef et al., Eds., Elsevier.
Ratledge, C. "The Potential of Microorganisms for Oil . . . " World Conference on Emerging Technologies . . . pp. 310–330 (1986).

(List continued on next page.)

*Primary Examiner*—Douglas W. Robinson
*Assistant Examiner*—Jon P. Weber
*Attorney, Agent, or Firm*—Banner, Birch, McKie & Beckett

[57] ABSTRACT

This invention relates to a process for producing a single cell edible oil containing DHA, to the oil itself and to uses for the oil. Marine microorganisms are cultivated in fermentors and induced to produce the single cell oil which subsequently is recovered by extraction with solvents.

25 Claims, 1 Drawing Sheet

OTHER PUBLICATIONS

Cox, E. R., "Dinoflagellates," *CRC Handbook of Microbiology* vol. II, pp. 489–501.

Tuttle, et al. "An optimal growth medium for the dinoflagellates Crypthecodinium..." *Phycologia* vol. 14(1) pp. 1–8 (1975).

Lands, *Fish and Human Health* (1986) Academic Press.

Harrington et al., "The Polyunsaturated Fatty Acids of Marine Dinoflagellates" *J. Protozool*, 17:213–219 (1970).

Guillard et al.: *Dinoflagellates*, (1984) Academic Press.

Crawford, *P.AOCS. Short Course on Polyunsaturated Fatty Acids and And Eicosanoids*, 270–295 (1987).

Gold et al., *Protozool*, 13:255–257 (1966).

Henderson et al., *Phytochemistry* 27:1679–1683 (1988).

Beach et al., *Biochemica et Biophysica Acta* 316:56–65 (1973).

Caspary, *Clinics in Gastroenterology*, 7:351–374 (1978).

Orcutt, et al., *Lipids* 9:1000–1003 (1974).

Guillard, *Culture of Marine Invertabrae Animals*, Smith et al. (eds.) 1975.

Kyle, et al., *Proc. Int. Symp. Diet. Lipids* 161–169 (1989).

Sorokin & Krauss, *The Natural Environmental Research Council*... (1958).

Beach et al., *BBA*; 316:56–69 (1973).

Beach et al., *BBA*, 369:16–24 (1974).

Ackman, in *Fats for the Future*, (R. C. Cambie, Ed.), pp. 189–203 (1980).

PRODUCTION OF DOCOSAHEXAENOIC ACID BY DINOFLAGELLATES

BACKGROUND OF THE INVENTION

This invention relates to edible, single-cell oil containing docosahexaenoic acid (DHA). The invention also relates to methods of producing such oil containing DIN in commercially viable yields and to products containing the oil.

DHA is an omega-3-fatty acid and is the most abundant long chain polyunsaturated fatty acid (PUFA) in the grey matter of the brain. Omega-3-fatty acids in general are known to be beneficial in reducing the incidence of coronary heart disease [Lands, *Fish and Human Health* (1986) Academic Press]. However, the metabolism of omega-3-fatty acids is not well understood. Thus, precise clinical dosages and efficacy remain unknown.

Cold water marine fish are a known source of omega-3-fatty acids, including DHA. U.S. Pat. No. 4,670,285 discloses the use of fish oil from fish such as menhaden and herring as a source of $C_{22}$ omega-3-fatty acids. Indeed, fish oils are the primary commercial source of omega-3-fatty acids. Often, however, fish oils are unusable for human consumption because of contamination with environmental pollutants such as PCB's.

There also are problems associated with the recovery of fish oils containing DHA. Such oils often have a fishy odor and unpleasant tastes associated with the acids. These tastes render the oils unsatisfactory for use in edible compositions such as baby food and infant formulas.

Marine microorganisms also are known to contain DHA. In particular, various species of dinoflagellates are known to contain DHA. Harrington et al., "The Polyunsaturated Fatty Acids of Marine Dinoflagellates" *J. Protozoal*, 17:213-219 (1970), characterize the fatty acid content of eight photosynthetic and one heterotrophic marine dinoflagellates, and conclude that the dinoflagellates are a primary producer group of docosahexaenoic acid and contribute substantial amounts of that compound to the marine food chain.

Successful cultivation of dinoflagellates to produce an edible oil containing DHA has not been achieved. Dinoflagellates in general are very slow growing and are shear sensitive. Guillard et al., *Dinoflagellates*, (1984) Academic Press. The prior art discloses that even a small amount of agitation in the culturing vessel reduces growth of the cultures. However, such agitation would be necessary to achieve adequate oxygenation in order to maximize growth for commercial production.

DHA is thought to be essential for the proper brain development of infants because, as noted above, it is the most abundant long chain PUFA in the brain. Although a metabolic pathway exists in mammals for the biosynthesis of DHA, this pathway is bioenergetically unfavorable [Crawford, P. *AOCS. Short Course in Polyunsaturated Fatty Acids and Eicosanoids*, pp. 270-295 (1987)] and mammals, like fish, are thought to obtain most of their DHA from dietary sources. In the case of infants, the most likely source would be human milk. Indeed, DHA is the most abundant PUFA in human milk. Generally, however, DHA is absent from infant formulas. U.S. Pat. No. 4,670,285 does disclose an infant formula containing omega-3-fatty acids. However, the acids utilized therein are obtained from fish oil and have associated therewith the unpleasant characteristics previously described. Furthermore, fish oils generally contain another omega-3-fatty acid, eicosapentaenoic acid (EPA), an undesirable component in infant formulas because of its prolonged anticoagulant effects.

Accordingly, it is an object of the present invention to provide a single-cell edible oil containing DHA. Preferably this oil will have no significant quantities of other polyunsaturated fatty acids (PUFA's), i.e. greater than about 2% of the total fatty acid content. In general, it is an object of the present invention to produce single-cell oil in commercially viable yields. The oil, characterized herein as a "designer" oil, after extraction can be used in infant formulas, baby foods, dietary supplements and pharmaceuticals.

In addition, it would be desirable to acquire further knowledge of the metabolic pathway of omega-3fatty acids. Isotopically labeled DHA would be of great utility in this regard. However, to date, no method has been known to produce abundant quantities of isotopically labelled DHA. Thus, it also is an object of the present invention to provide isotopically labeled DHA in sufficient quantities to undertake such research.

SUMMARY OF THE INVENTION

The present invention relates to the cultivation of microorganisms, notably dinoflagellates, in a fermentor, induction of those microorganisms to produce significant quantities of single cell oil containing a high proportion of DHA and recovery of that oil. As used herein, "single cell oil" refers to a triglyceride product of a unicellular organism. The present invention also includes mutant organisms capable of producing enhanced quantities of single-cell oil containing at least about 20% by weight DHA and includes single cell oil containing DHA.

The present invention provides an economical method of obtaining enhanced levels of edible oils containing DHA. Additionally, the method permits the commercial cultivation of dinoflagellates in elevated cell densities.

Edible oils produced by the method of this invention lack unpleasant tastes and fishy odors and also are free of environmental contaminants often found in DHA-containing oils from conventional sources. Accordingly, the present invention further includes food products containing the oil of this invention.

DETAILED DESCRIPTION OF THE BEST MODE OF PRACTICING THE INVENTION

Figure 1:
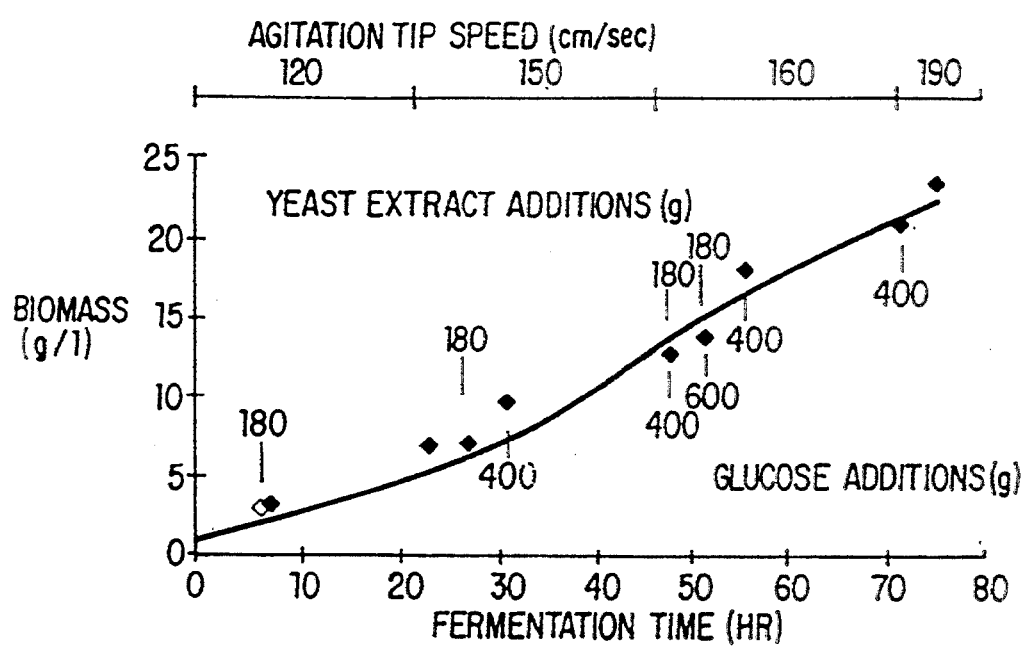
FIG. 1 is a graphic illustration of *C. cohnii* biomass accumulation over time with the addition of various nutrients.

In accordance with the present invention, microorganisms capable of producing a single cell oil containing DHA are cultivated in a fermentor in a nutrient solution capable of supporting the growth of such organisms. Preferably the single cell oil will contain at least about 20% by weight DHA.

Any microorganisms capable of producing a single-cell edible oil containing DHA can be used in the present invention. For example, photosynthetic diatoms can be used. Preferred microorganisms are marine dinoflagellates, including *Crypthecodinium sp.* Especially preferred is *Crypthecodinium cohnii*, an obligate heterotroph requiring a reduced carbon source for growth. *C. cohnii* is preferred because it contains a fatty acid profile in which DHA is the only PUFA present in sufficient quantities (greater than about 1% of the total amount of PUFAs). Samples of this organism, designated MK8840, have been deposited with the American Type Culture Collection at Rockville, Maryland, and assigned accession number 40750. As used herein, microorganism, or any specific type of microorganism, includes wild strains, mutants or recombinant types. Any microorganism which produces enhanced levels of oil containing DHA is considered to be within the scope of this invention. One of the features of the present invention is its recognition of the edible oil-producing capability of microorganisms such as dinoflagellates and the attendant solution to the problem of maintaining a reliable, economic source of such oils. Accordingly, wild-type and recombinant microorganisms designed to produce single cell oil containing DHA are an aspect of this invention. Such recombinant organisms would include those designed to produce greater quantities of DHA in the single cell oil, greater quantities of total oil, or both, as compared to the quantities produced by the same wild type microorganism, when provided with the same substrates. Also included would be microorganisms designed to efficiently use more cost-effective substrates while producing the same amount of single cell oil containing DHA as the comparable wild-type microorganism.

In general, those of skill in the art would not consider *C. cohnii* a suitable organism for cultivation in a fermentor. Previous workers have commented on the extremely complex mixture of nutrients required to successfully cultivate *C. cohnii*. Gold et al. *Protozoal*, 13:255–257 (1966); Guillard, et al. in "Dinoflagellates", Academic Press (1984); Henderson, et al., *Phytochemistry* 27:1679–1683 (1988). In contrast, the present invention achieves the cultivation of DHA-producing microorganisms in a simple medium containing glucose and yeast extract. Use of these components in a solution such as seawater provides economically significant growth rates and cell densities. For example, during the course of a 3–5 day fermentation, *C. cohnii* cell densities of at least 10 grams of biomass per liter of solution, and typically from 20 to about 40 grams per liter, can be attained. Such densities have not heretofore been attainable.

Although cultivation can occur in any suitable fermentor, preferably the organism is grown either in a stirred tank fermentor (STF) or in an air lift fermentor (ALF), both types known to those of skill in the art. When a STF is selected, agitation is provided using either Rushton-type high efficiency turbines or pitched-blade or marine impellers. Agitation and duration renews the supply of oxygen to the microorganisms. The rate of agitation normally is increased as the biomass increases, due to the increased demand for oxygen. It is desirable to keep the tip speed at not greater than about 500 cm/sec. Selection of strains of microorganisms which are capable of withstanding greater tip speeds without undergoing shear is within the purview of those of skill in the art. The use of such strains is expressly included in this invention.

As noted above, seawater is an acceptable medium for the nutrient solution. The seawater can be either natural, filtered or an artificial mix, each of which can be diluted to ¼ strength with tap water or concentrated to 2 times normal strength. A preferred example is Instant Ocean ® (IO) brand artificial seawater. Although *C. cohnii* is a marine microorganism, some growth has been observed in zero salinity. The use of variants which grow well in reduced salinities is specifically encompassed by this invention. Micronutrients can be added and may be required. However, such micronutrients are known to those of skill in the art and generally are present in seawater or tap water. If the organism selected is heterotrophic, such as *C. cohnii*, then a carbon source is added.

Preferably, after addition of the seawater medium to the fermentor, the fermentor containing the medium is sterilized and cooled prior to adding the nutrients and a seeding population of microorganism. (Although it is acceptable to sterilize the nutrients together with the seawater, sterilization in this manner can result in a loss of available glucose.) The nutrients and microorganism can be added simultaneously or sequentially.

An effective seed concentration can be determined by those of skill in the art. When a STF is used, the addition of a population of from about 0.05 to 1.0 grams of dry weight equivalent per liter at the beginning of the fermentation is preferred. This is about $10^5$ cells per ml. Thus, for a 30 liter fermentor, 1.5 liters of seeding media, containing viable cells at a density of 20 g dry weight per liter would be added.

Oxygen levels preferably are maintained at a D.O. of at least about 10% of air saturation level. Biosynthesis of DHA requires oxygen and, accordingly, higher yields of DHA require D.O. levels at from about 10% to 50% of air saturation levels. Agitation tip speeds of 150–200 cm/sec in combination with an aeration rate of 1VVM (volume of air/volume of fermentor per minute) provides D.O. levels of from about 20% to about 30% at biomass densities of about 25 g dry weight/liter of culture. Higher cell densities may require higher D.O. levels, which can be attained by increased aeration rates by $O_2$ sparging, or by increasing the air pressure in the fermentor.

Acceptable carbon sources are known to those of skill in the art. For example, carbon can be provided to *C. cohnii* in the form of glucose. Other heterotrophs can use other reduced carbon sources, a matter easily determined by those of skill in the art, and autotrophs utilize carbon dioxide. *C. cohnii* will also grow on other reduced, more complex, carbon sources. Typically, a fermentation is initiated with about 10–20 g/liter glucose. More glucose is added during the fermentation as required. Alternatively, from about 80 to 150 g glucose/liter initially can be added, thereby minimizing the frequency of future additions. If glucose levels drop to zero, the culture can die within a few hours. The amount of carbon source provided to other organisms can readily be determined by those of skill in the art.

In addition to a reduced carbon source, a nitrogen source, such as yeast extract (YE), is provided to the medium. Commercially available yeast extract is acceptable. For example, DIFCO brand yeast extract can be used. The yeast extract is an organic nitrogen source also containing micronutrients. Other organic nitrogen sources can easily be determined by those of skill in the art. However, such compounds are more expensive than yeast extract. The use of variants capable of growing on urea or nitrates is within the scope of this invention. Typically, the fermentation is initiated with about 4–8 g YE/liter. More YE can be added as required. A typical fermentation run requires from about 25 to 50 g YE/liter over the course of the run. Accordingly, that amount of YE can be added initially with a reduced need for further additions. The precise amount can be determined by those of skill in the art.

The cultivation can be carried out at any life-sustaining temperature. Generally *C. cohnii* will grow at temperatures ranging from about 15° C. to 34° C. Preferably the temperature is maintained at about 20°–28° C. Strains which grow at higher temperatures are preferred, because they will have a faster doubling time, thereby reducing the fermentation time. Appropriate temperature ranges for other microorganisms are readily determined by those of skill in the art.

The cultivation can be carried out over a broad pH range, typically from about pH 5.0 to 9.0. Preferably, a pH range of from about 7.0 to about 7.8 is used. The initial growth tends to acidify the medium. Addition of a base, such as KOH or NaOH, corrects this acidification. During the later stages of the fermentation, the culture medium tends to become alkaline. The addition of YE ordinarily is sufficient to maintain the pH in the desired range. However, if desired, inorganic acid pH controls can be used to correct alkalinity.

Production of the single cell oil is induced in the dinoflagellates by the imposition of a nitrogen deficiency. Such deficiencies are caused by providing YE in a limiting amount such that the medium runs out of YE while available glucose remains. The present invention recognizes that it is the carbon source to nitrogen source ratio which promotes the efficient production of the single cell oil. Using glucose and YE as exemplary, a preferred ratio of carbon source to nitrogen source is about 2–4 parts glucose to 1 part YE. Similar ratios for other carbon and nitrogen sources can be calculated by those of skill in the art.

After induction of oil production, the culture is grown for about 24 additional hours. During this period of oleosynthesis, the single cell oil containing DHA is being synthesized and visible oil droplets become apparent. Those of skill in the art can readily calculate the time of fermentation required to achieve the expected amount of cell biomass based upon the added amount of YE. When that time has passed, the culture is grown for an additional 24 hours and harvested. In general the *C. cohnii* are cultivated for a time sufficient to produce single cell oil, usually from about 60 to about 90 hours, although this time is subject to variation.

From about 20 to 30% of the resultant biomass, using wild-type *C. cohnii*, comprises extractable oil. Strain selection can increase this percentage and such selection is within the scope of this invention. Preferably, the oil comprises greater than about 90% triglycerides having, in general, the following fatty acid composition.

15–20% myristic acid ($C_{14:0}$)
20–25% palmitic acid ($C_{16:0}$)
10–15% oleic acid ($C_{18:1}$)
40–45% DHA ($C_{22:6}$)
0–5% others The crude oil is characterized by a yellow-orange color and is liquid at room temperature. Desirably, the oil contains at least about 20% DHA by weight and most preferably at least about 35% DHA by weight.

The organisms are harvested by conventional means, known to those of skill in the art, such as centrifugation, flocculation or filtration, and can be processed immediately or dried for future processing. In either event, the oil can be extracted readily with an effective amount of solvent. Suitable solvents can be determined by those of skill in the art. However, a preferred solvent is pure hexane. A suitable ratio of hexane to dry biomass is about 4 liters of hexane per kilogram of dry biomass. The hexane preferably is mixed with the biomass in a stirred reaction vessel at a temperature of about 50° C. for about 2 hours. After mixing, the biomass is filtered and separated from the hexane containing the oil. The residual biomass, i.e. the single cell edible oil extracted biomass of the microorganisms, such as *C. cohnii*, can be used as an animal feed, containing as it does about 35–40% protein, 8–10% ash and 45–50% carbohydrates. The hexane then is removed from the oil by distillation techniques known to those of skill in the art. Conventional oilseed processing equipment is suitable to perform the filtering, separation and distillation. Additional processing steps, known to those of skill in the art, can be performed if required or desirable for a particular application. These steps also will be similar to those involved in conventional vegetable oil processing and do not comprise a part of this invention.

Isotopically labelled single cell oils, including labeled DHA, can be easily obtained in sufficient quantities to permit research into the metabolic pathways of DHA by the method of this invention. When $^{13}$C-glucose or $^{14}$C-glucose is provided as the reduced carbon substrate, labeled DHA results.

The present invention also includes food products, such as infant formulas and baby foods, as well as dietary supplements, which contain the single-cell oil containing DHA of the present invention. While those of skill in the art have recognized that infant formulas containing DHA are desirable, the prior art infant formulas contained DHA from fish oil, with its attendant unpleasant tastes and organoleptic characteristics. Furthermore, fish oil supplementation of infant formula includes the addition of eicosapentaenoic acid (EPA), an omega-3-fatty acid known to possess anticoagulant activity. Such an activity is not desirable in infant formula or baby food and the single cell oil described herein contains no significant quantity of EPA. Food products, such as infant formula, containing the single cell oil of the present invention do not have the unpleasant organoleptic characteristics of fish oil. The food products thus are more readily accepted by infants and adults alike. Preferably the infant formula of the present invention contains about 0.05% by weight of single cell oil containing DHA. The baby food of the present invention, having a more solid constitution, preferably contains about 0.5% by weight of single cell oil containing DHA. In both instances, most preferably, the oil contains at least about 35% DHA.

The present invention includes pharmaceutical products including single cell oil containing DHA. Preferably the products contain at least about 35% DHA. Exemplary of such pharmaceutical products is one suitable for use in providing parenteral nutrition to infants. Additionally, dietary supplements containing the single cell oil are encompassed. Preferably, such supplements are in the form of gelatin capsules encapsulating said oil.

The present invention also includes single cell oil containing DHA. Preferably the single cell oil contains at least about 20% by weight DHA. Most preferably the oil contains at least about 35% by weight DHA.

The present invention having been generally described, reference is had to the following non-limiting specific example.

EXAMPLE

Into a 30-liter working volume STF was loaded a medium of one quarter strength artificial seawater. Six liters of IO were combined with 18 liters of tap water. The fermentor containing the medium was sterilized and cooled to 28° C. Four hundred ml of concentrated YE (455 g/l), 900 ml of glucose syrup (400 g/l) and one liter of inoculum from a seed fermentor containing about $2 \times 10^7$ cells/ml or a biomass of 20 g/liter (yielding a final concentration of about $10^5$ cells/ml or a biomass of about 700 mg/liter), were added to the medium. Agitation was set at 120 cm/sec tip speed and aeration was set at 1 VVM (30 liters per minute). Additional glucose syrup (900 ml) was added after 30 hours and another 4.2 liters over the next 42 hours. Thus 6 liters of glucose syrup were added in total. Concentrated YE solution (400 ml) was added at hour 6 and another 1.2 liters were added over the next 48 hours until a total of 2.0 liters had been added. To maintain the D.O. at greater than 20%, at 24 hours the agitation tip speed was increased to 150 cm/sec and at 48 hours to 160 cm/sec. At 72 hours, the tip speed was increased to 200 cm/sec and the culture was permitted to grow for an additional time sufficient to convert the final charge of glucose into cellular oil. The culture was then harvested by centrifugation with the cell pellet retained. The harvested pellet of cells was frozen and dried (lyophilized) to about a 4% moisture content. Hexane (2.8 liters) was added to the dried biomass and stirred in a glass kettle for 1.5 hours at 50° C. A rotary evaporator was used to remove the hexane, producing about 175 g of crude DHA-containing oil.

We claim:

1. A method of producing a single cell edible oil containing at least about 20% docosahexaenoic acid (DHA) in triglyceride form comprising:
   cultivating heterotrophic microalgae of the class Dinophyceae capable of producing said single cell oil in an aerated fermentor containing a nutrient solution having a limiting nitrogen source and an oxygen level of at least about 10% of air saturation level and continuing cultivation to achieve a cell density of at least about 10 grams biomass per liter of nutrient solution,
   wherein the concentration of the nitrogen source in the nutrient solution is limited sufficiently to induce said microalgae to produce the single cell oil at a concentration of at least about 2 grams per liter of nutrient solution, and
   recovering said single cell oil.

2. The method of claim 1, wherein the microalgae is of the genus Crypthecodinium.

3. The method of claim 2, wherein said microalgae comprises *Crypthecodinium cohnii*.

4. The method of claim 3, wherein said nutrient solution comprises seawater.

5. The method of claim 4, wherein said seawater comprises an artificial seawater.

6. The method of claim 5, wherein said nutrient solution comprises a one-quarter strength solution of artificial seawater.

7. The method of claim 4, wherein said nutrient solution further comprises a reduced carbon source.

8. The method of claim 7, wherein said reduced carbon source comprises glucose.

9. The method of claim 4, wherein said limiting nutrient comprises an organic nitrogen source.

10. The method of claim 9, wherein said nitrogen source comprises yeast extract.

11. The process of claim 10, wherein the ratio of said glucose to said yeast extract is from about 2 to 4 parts glucose to 1 part yeast extract.

12. The method of claim 11, further comprising maintaining a dissolved oxygen content at a range of from about 10% to about 50% of air saturation.

13. The method of claim 12, wherein said range is from about 20-30%.

14. The method of claim 13, wherein said fermentor is a stirred tank fermentor having a turbine.

15. The method of claim 14, wherein said turbine agitates said nutrient solution, thereby providing oxygen to said microalgae.

16. The method of claim 1, wherein said aerated fermentor is aerated at a rate of 1 volume of air per volume of fermentor per minute.

17. The method of claim 1, wherein said nutrient solution comprises $^{13}$C-glucose or $^{14}$C-glucose.

18. The method of claim 1, wherein the microalgae is cultivated to a density of at least about 20 g/liter of nutrient solution.

19. A method for the production of a single-cell-edible oil containing at least 20% DHA in triglyceride form and lacking a fishy taste comprising:
   a) adding to a fermentor initially containing a nutrient solution comprising about one-quarter strength artificial seawater, 1-2% glucose and 0.4-0.8% yeast extract, about 0.5-1.0 g dry wt/liter (about $10^5$ cells/ml) of *C. cohnii*,
   b) cultivating said *C. cohnii* at a temperature of from about 15° C. to about 34° C. and a pH of from about 5.0 to 9.0,
   c) incrementally adding glucose and yeast extract to said nutrient solution for about 56 hours,
   d) adding additional glucose to said nutrient solution for about 16 additional hours to induce said *C. cohnii* to produce a single-cell edible oil,
   e) maintaining a dissolved oxygen content of about 20-30% of air saturation level throughout said cultivation,
   f) harvesting said *C. cohnii* after about 60 to 90 hours, and
   g) recovering said single-cell edible oil.

20. The process of claim 19, further comprising extracting said single cell edible oil from said *C.cohnii*.

21. The process of claim 20, wherein said extraction is by treatment with a solvent such that said oil is extracted into said solvent.

22. The process of claim 21, wherein said solvent comprises hexane.

23. The process of claim 22, wherein said hexane is applied to said *C. cohnii* at a rate of about 4 liters per kilogram of dry biomass of said *C. cohnii* and is mixed with said biomass in a stirred reaction vessel for about 2 hours at about 50° C.

24. The process of claim 23, further comprising filtering said hexane containing extracted oil from said biomass and then removing said hexane by distillation from said oil.

25. A single cell-edible oil comprising at least 20% docosahexaenoic acid in triglyceride form, said oil produced according to the method of claim 1 or the method of claim 19.

* * * * *